United States Patent
Ng et al.

(10) Patent No.: US 9,572,517 B2
(45) Date of Patent: Feb. 21, 2017

(54) BABY MONITORING MAT BASED ON FIBER OPTIC SENSOR

(75) Inventors: Seng Tat Ng, Singapore (SG); Xin Jiang, Singapore (SG); Hwee Siong Chong, Singapore (SG)

(73) Assignee: Ospicon Company Limited, Hong Kong (HK)

( * ) Notice: Subject to any disclaimer, the term of this patent is extended or adjusted under 35 U.S.C. 154(b) by 853 days.

(21) Appl. No.: 13/700,660

(22) PCT Filed: Mar. 3, 2011

(86) PCT No.: PCT/SG2011/000083
§ 371 (c)(1),
(2), (4) Date: Jan. 17, 2013

(87) PCT Pub. No.: WO2012/118440
PCT Pub. Date: Sep. 7, 2012

(65) Prior Publication Data
US 2013/0109931 A1    May 2, 2013

(51) Int. Cl.
*A61B 5/08* (2006.01)
*A47D 15/00* (2006.01)
(Continued)

(52) U.S. Cl.
CPC ........... *A61B 5/0816* (2013.01); *A47D 15/003* (2013.01); *A61B 5/0059* (2013.01); *A61B 5/1128* (2013.01);
(Continued)

(58) Field of Classification Search
CPC ....... A61B 5/0059; A61B 5/07; A61B 5/6891; A61B 5/7282; A61B 2562/0233; A61B 5/04; A61B 5/14557; A61B 5/70; A61B 5/721; A61B 1/0684; A61B 2562/0242; A61B 5/0261; A61B 5/08; A61B 5/0816; A61B 5/097; A61B 5/11; A61B 5/1118; A61B 5/1126; A61B 5/1455; A61B 5/6804; A61B 5/6831; A61B 5/6892; A61N 1/02; A61N 2005/0652; A61N 5/06; A61N 5/0613; A61N 2005/0626; A61N 2005/063; A61N 2005/0632; A61N 2005/0635; A61N 2005/065; A61N 2005/0651; A61N 2005/0664; G08B 21/0461; A47D 15/003; G01L 1/242
See application file for complete search history.

(56) References Cited

U.S. PATENT DOCUMENTS 6,498,652 B1   12/2002   Varshneya
7,825,814 B2   11/2010   Lokhorst
(Continued)

FOREIGN PATENT DOCUMENTS

CN   1612174 A      5/2005
CN   201361029 Y   12/2009
(Continued)

OTHER PUBLICATIONS

International Search Report from corresponding International Application No. PCT/SG2011/000083, 3 pages, Oct. 6, 2011.
Written Opinion from corresponding International Application No. PCT/SG2011/000083, 6 pages, Oct. 6, 2011.
ISR, PCT/SG2011/000083, Mar. 3, 2011.

Primary Examiner — Deborah Malamud

(57) ABSTRACT

A Baby Monitoring Mat is provided having a top mesh layer, a bottom mesh layer, two flexible sheets, and an optical cable. The optical cable can be routed between the top mesh layer and the bottom mesh layer. The flexible sheets are also between the top mesh layer and the bottom mesh layer forming a sensing area. A light source is provided for feeding light from one side of the optical cable to a photodiode for detecting light attenuation at the other end of the optical cable. A processor receives signals from the light source and photodiode and the signals are processed to
(Continued)

determine movements and breath counts. The signals are generated based on the light attenuation changes along the optical fiber cable detected by photodiode. A method for monitoring baby on a mat is also provided.

9 Claims, 16 Drawing Sheets

(51) Int. Cl.
*A61B 5/00* (2006.01)
*A61B 5/11* (2006.01)
*G01L 1/24* (2006.01)

(52) U.S. Cl.
CPC ........... *A61B 5/6807* (2013.01); *A61B 5/6892* (2013.01); *A61B 5/7278* (2013.01); *A61B 5/7282* (2013.01); *A61B 5/746* (2013.01); *A61B 5/7455* (2013.01); *G01L 1/242* (2013.01)

(56) References Cited

U.S. PATENT DOCUMENTS

| | | |
|---|---|---|
| 2007/0149883 A1 | 6/2007 | Yesha |
| 2008/0219464 A1* | 9/2008 | Smith ..................... A61B 7/04 381/67 |

FOREIGN PATENT DOCUMENTS

| | | |
|---|---|---|
| EP | 2243422 A1 | 10/2010 |
| JP | 2005184772 A | 7/2005 |
| JP | 2005532854 A | 11/2005 |
| JP | 2005334283 A | 12/2005 |
| JP | 2006-043445 | 2/2006 |
| JP | 2007144070 A | 6/2007 |
| JP | 2010131340 A | 6/2010 |
| KR | 20-2008-0005473 | 11/2008 |
| KR | 20080005473 U | 11/2008 |
| WO | WO2011016778 A1 | 2/2011 |

* cited by examiner

217 : Fiber cable assembly
222 : Flexible bridge
240 : Water proof cover
241 : Top layer latex
220 : Top layer mesh (Right)
221 : Bottom layer mesh (Left)
242 : Bottom layer latex
800 : Sensor box assembly
911 : Electronics box top housing
912 : Electronics box printed circuit board
913 : Electronics box bottom housing
224 : Top layer mesh (Left)
225 : Bottom layer mesh (Right)

BABY MONITORING MAT BASED ON FIBER OPTIC SENSOR

PRIORITY CLAIM

This application claims the benefit of priority from International Application No. PCT/SG2011/000083, filed Mar. 3, 2011, which is incorporated by reference.

FIELD OF INVENTION

This patent invention relates to baby monitoring mats that utilize optic sensing systems for the detection of presence of baby, as well as movement and breath count thereof.

BACKGROUND

Currently, there are products in the consumer market that can detect baby-breathing movement using different sensing technology.

One method is based on piezoresistive pressure sensor pads that are placed beneath the mattress for detecting movements. This type of pressure sensor pad may include a micro-machined silicon diaphragm with piezoresistive strain gauges diffused into it, such as fused to a silicon or glass backplate. Pressure induced strain increases the value of the radial resistance. This resistance change can be high as 30%. The resistors are connected as a Wheatstone Bridge Circuit, the output of which is directly proportional to the pressure applied to the pressure sensor pads.

The pressure sensor pads may detect movement of the baby sleeping on the mattress, including breathing action by baby. But such sensors often provide false alarms that may arise from high sensitivity of the pressure sensor pad to any surrounding vibrations transmitted to the pressure sensor through the bed frame structure. Further, such pressure pad would not work properly on a spring-based mattress. In addition, although such pressure sensor pad is also able to pick up breathing action, it does not provide any breath count because it is not able to differentiate the type of movements occurring on the bed.

There exists another sensor that is based on the properties of piezo film (strip of piezoelectric PVDF polymer film) as a dynamic strain sensor to detect the breathing rate of an infant. Such sensor uses a PVDF-monitor device clipped to the waistband of the baby's diaper. When the baby breathes, its stomach movement causes strain to the piezo film materials, which generates the signal for detecting breathing movements. Such a sensor, however, also provides false alarms arising from bad contact between a diaper or nappy and a body of a baby, especially if the baby body circumference is small or the diaper or nappy is too large or too loose for the baby. Further, such a sensor is also not able to provide any breath count; only detects for non-breath movement.

SUMMARY

In one aspect of the present invention, there is provided, a baby monitoring mat that includes of a sensor mat having a top mesh layer, a bottom mesh layer, and two flexible sheets and an optical cable, wherein the optical cable is routed across and sandwiched in between the top mesh layer and the bottom mesh layer, and the flexible sheets further sandwiched the top mesh layer and the bottom mesh layer in between forming a sensing area across the flexible sheet surface; a light source for feeding light from one side of the optical cable; a photodiode for detecting light attenuation at the other end of the optical cable; a printed circuit board having a processor connected to the light source and the photodiode, wherein the processor operationally receives signals from the photodiode, the signals are processed to determine movements and breath counts. The signals are generated based on the light attenuation changes along the optical fiber cable detected by a photodiode, the light attenuation changes are operationally caused by the optical fiber bending lost caused by baby movements and breath.

In one embodiment, the light source is a light emitting diode. The flexible sheets may be latex sheets. It is desired that the optical fiber cable maybe a multimode optical fiber cable. Further, the top and bottom mesh layer may include grid patterns adapted to guide and protect the multimode optical fiber cable routed in a symmetrical manner across the sensor mat. The optical fiber cable may be spaced at least about 20 mm apart. In another embodiment, the top and bottom layer of mesh includes a symmetrical grid pattern spaced at least about 5 mm and less than about 8 mm apart with fiber turning hooks with spacing of about 20 mm apart to guide the multimode optical fiber across the sensor mat.

In a further embodiment, the baby monitoring mat may further include a flexible bridge for connecting two sandwiched mesh layers for allowing the baby monitoring mat to be foldable.

In another embodiment, the baby monitoring mat may further include a wireless transceiver on the printed circuit board, wherein the wireless transceiver operably transmits status information, such as baby presence and movement and breath counts, to a remote display unit, such that the movements on the sensor mat can be monitored there through.

Yet, the baby monitoring mat may further include a baby wake up sock electrically connected to the printed circuit board, the wake up sock is wearable on a baby's leg, wherein the wake up sock vibrates when the sensor detects zero breath count when a baby is presence on the sensor mat.

In another aspect of the present invention, there is also provided, a method of detecting movements and breath counts of a baby on a mat. The method includes providing an optical cable for routing across and sandwiched between the mats; and detecting movements on the mat through acquiring light attenuation changes along the optical fiber cable, wherein the light attenuation changes are operationally caused by the optical fiber bending lost caused by movements and breath on the mat.

There is yet another aspect of the present invention, that is, a method for monitoring a baby's movement and breath counts on a baby monitoring mat according to the aforesaid method, wherein a baby monitoring mat is configured according to the aforesaid specifications.

BRIEF DESCRIPTION OF THE DRAWINGS

The invention is described by way of non-limiting embodiments with reference to the accompanying FIGURES, in which.

DETAILED DESCRIPTION

Figure 1:
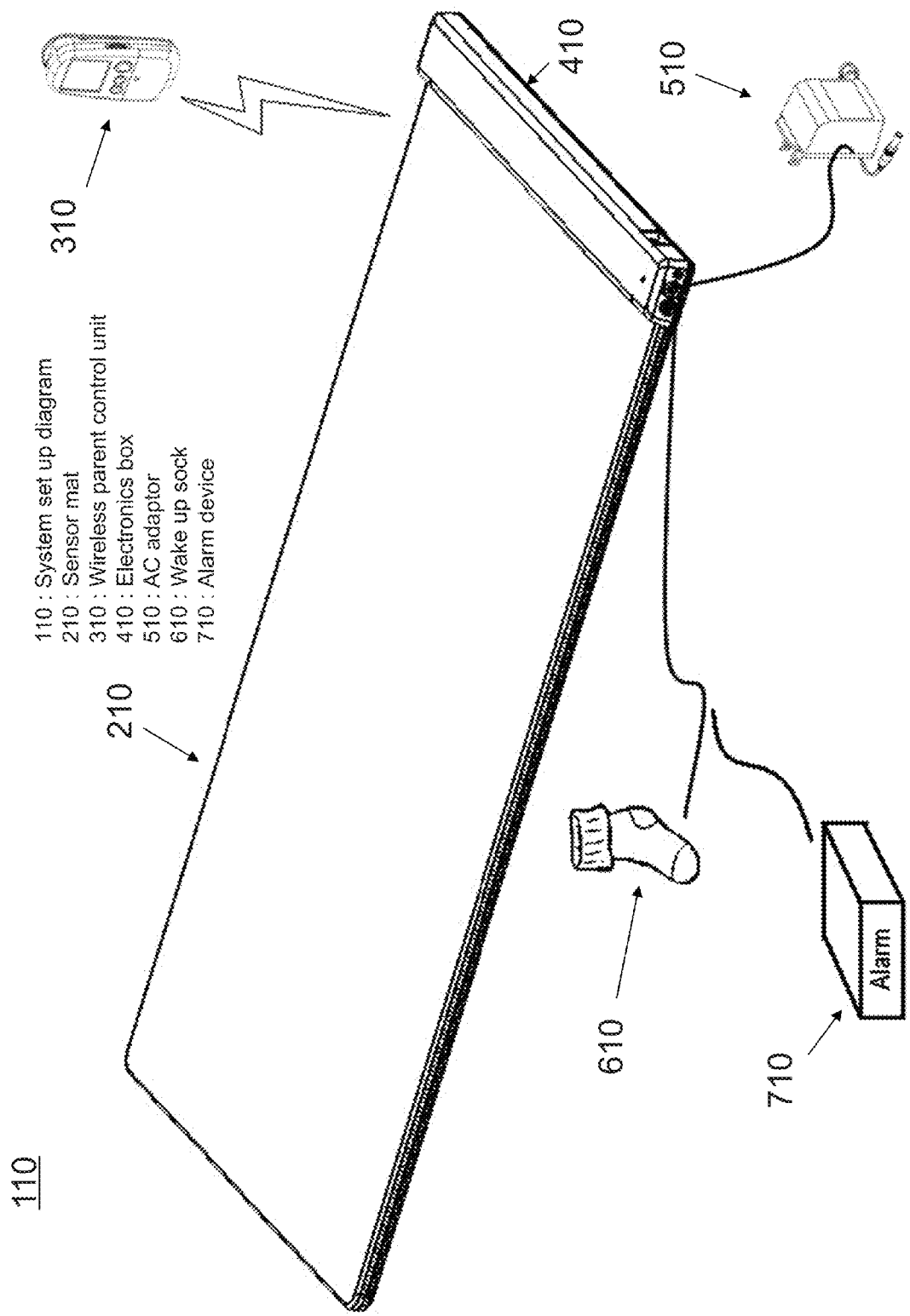
FIG. 1 is an overall system of a baby monitoring mat in accordance with one embodiment of the present invention.

The following descriptions of a number of specific and alternative embodiments are provided to understand the inventive features of the present invention. It shall be apparent to one skilled in the art that this invention may be practiced without such specific details. Some of the details may not be described in length so as to not obscure the invention. For ease of reference, common reference numerals will be used throughout the figures when referring to same or similar features common to the figures.

Figure 13:
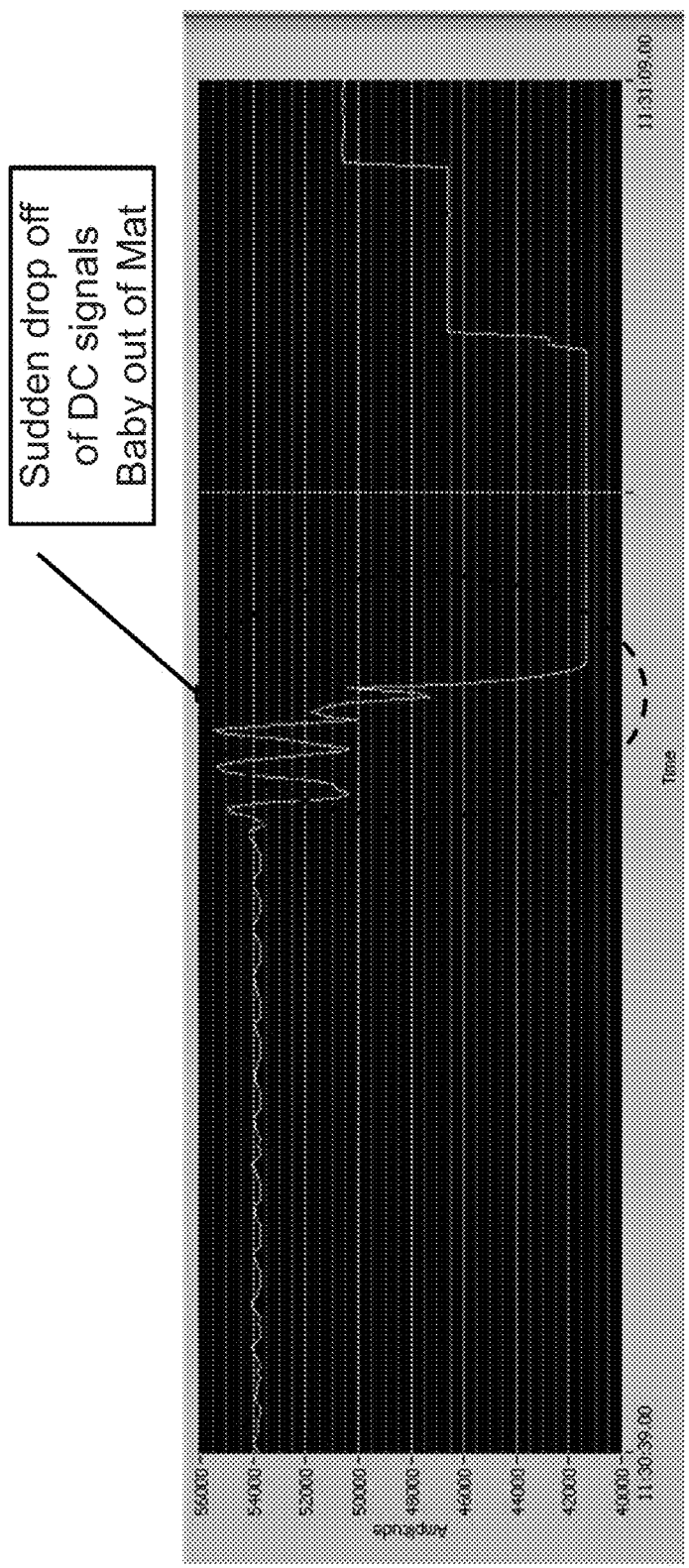
FIG. 13 exemplifies signal patterns for Baby presence detection.
Figure 14:
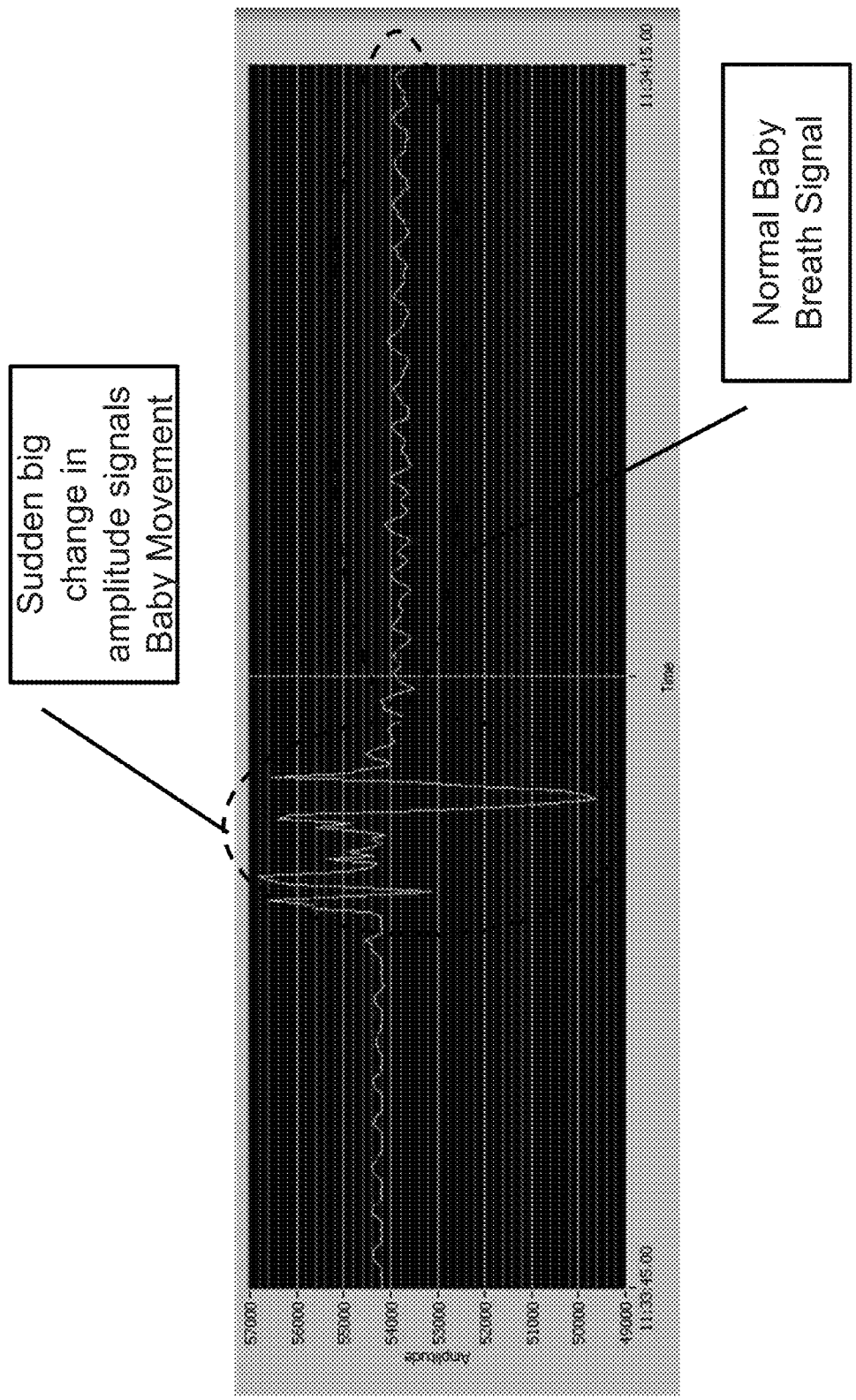
FIG. 14 exemplifies signal patterns for Baby movement detection.
Figure 15:
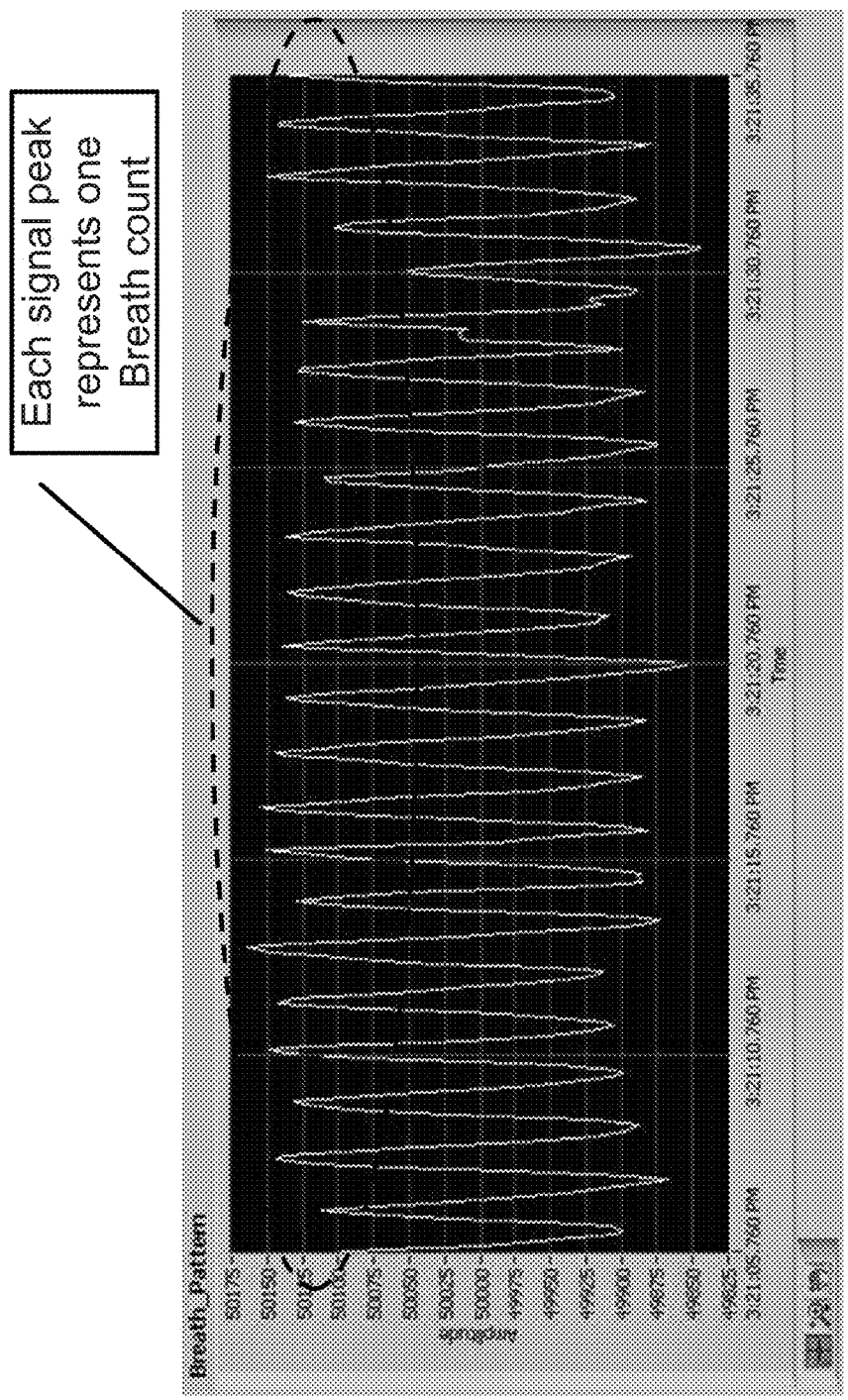
FIG. 15 exemplifies signal patterns for Baby Breath count detection.
Figure 16:
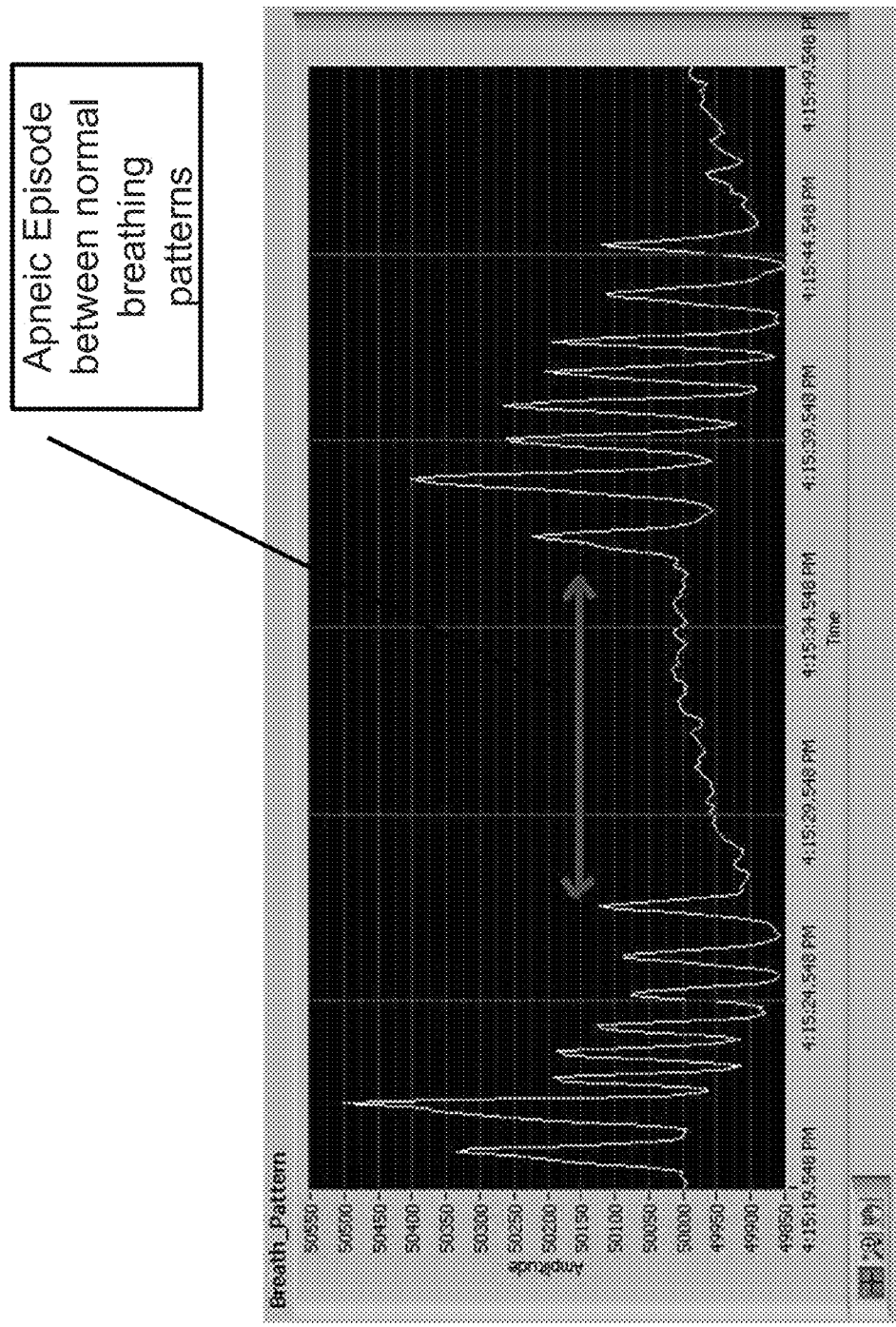
FIG. 16 exemplifies signal patterns for Baby Apneic Episode.

The present invention discloses an optic fiber sensor embedded to a baby mat in accordance with one embodiment of the present invention. The fiber cable is routed within a sandwiched structure inside the baby mat. Non-coherent light source is coupled into the fiber cable for operationally emitting light for travelling along the length of the fiber cable. Baby breathing movement on top of the mat will cause light lost due to internal reflections from the macro bending lost caused by the sandwiched structure. These reflections will create distinct light attenuation pattern when measured with a light detector. By processing the light attenuation signal pattern detected through the light detector, detection of movement, breath count and presence of the baby on the mat can be differentiated. FIGS. 13 to 16 illustrates signal patterns generated by the mat for the purposes of detecting Baby presence, movement, breath count and apneic episodes. FIG. 15 shows the signal of breathing movement, which is characterized by a periodic sine wave of certain constant amplitude and duration. The duration determines the breath/minute measurements. FIG. 16 shows the phenomena of an apneic episode whereby there are no breath cycles in between. An apneic episode that will generate an alarm is classified as 15 seconds of no breath cycles. FIG. 14 shows movement disturbances in between breathing cycles. A movement event is determined when the amplitude of the signal changes at least 6 times more than the amplitude of normal breath cycles for a period of at least 5 seconds. FIG. 13 shows the event of out of mat detection. An amplitude drop of at least 8000 in value signifies an out of mat event.

The optic fiber sensor of the above embodiment, provides an improved mechanical coupling whereby the full weight of the baby comes into direct contact with the mat without a mattress in between which can cause unnecessary interference to the accuracy of the sensing. Further, the sensitivity of the fiber sensor has improved over the conventional pressure sensor or the like because it is based on macro bending of light passing through the fiber. It advantageously provides the capability of measuring baby breath count, movement and presence accurately. The baby mat can be light in weight and portable to be used in different environments.

The baby monitoring mat is typically placed in the baby cot on top of the mattress. The mat can be powered by battery or AC/DC adaptor connected to the mat. When powered by a battery, the mat is portable and can be brought out to monitor the baby outside of the baby cot.

With reference to FIG. 1, a baby monitoring mat includes a Sensor Mat 210, an Electronic Box 410 and a Parent Control Unit 310. The entire area of the Sensor Mat has optical fiber cable embedded in between to enable detection of baby presence and movement and breath count when baby is placed on it. The Electronic Box 410 can be powered by an external AC/DC adaptor 510 and/or with battery installed inside the Electronic Box 410. An external alarm device 710 can be connected to the mat to provide additional notification of critical events detected by the Sensor Mat 210. A stimulation device in the form of a wake up sock 610, for example, can also be attached to the electronic box 410. The wake up sock 610 is integrated with a built-in vibrator, which will jolt the baby's feet when zero breath count or any predetermined condition is detected. The wake up sock 610 attempts to agitate the baby to resume normal breathing pattern while the caregiver is being notified to response to the baby's need via the Parent Control Unit 310. The Parent Control Unit 310 is operationally communicating with the Electronic Box 410 wirelessly. It has a display to indicate events such as Baby out of mat/presence, Baby movement and Baby Breath count continuously. Alarm of events detected by the sensor mat 210 is indicated with an audible alarm or vibration of the Parent Control Unit 310 working within the wireless range. When Parent Control Unit 310 is outside the wireless range of the baby monitoring mat, an out of range alarm will be sounded.

Figure 2:
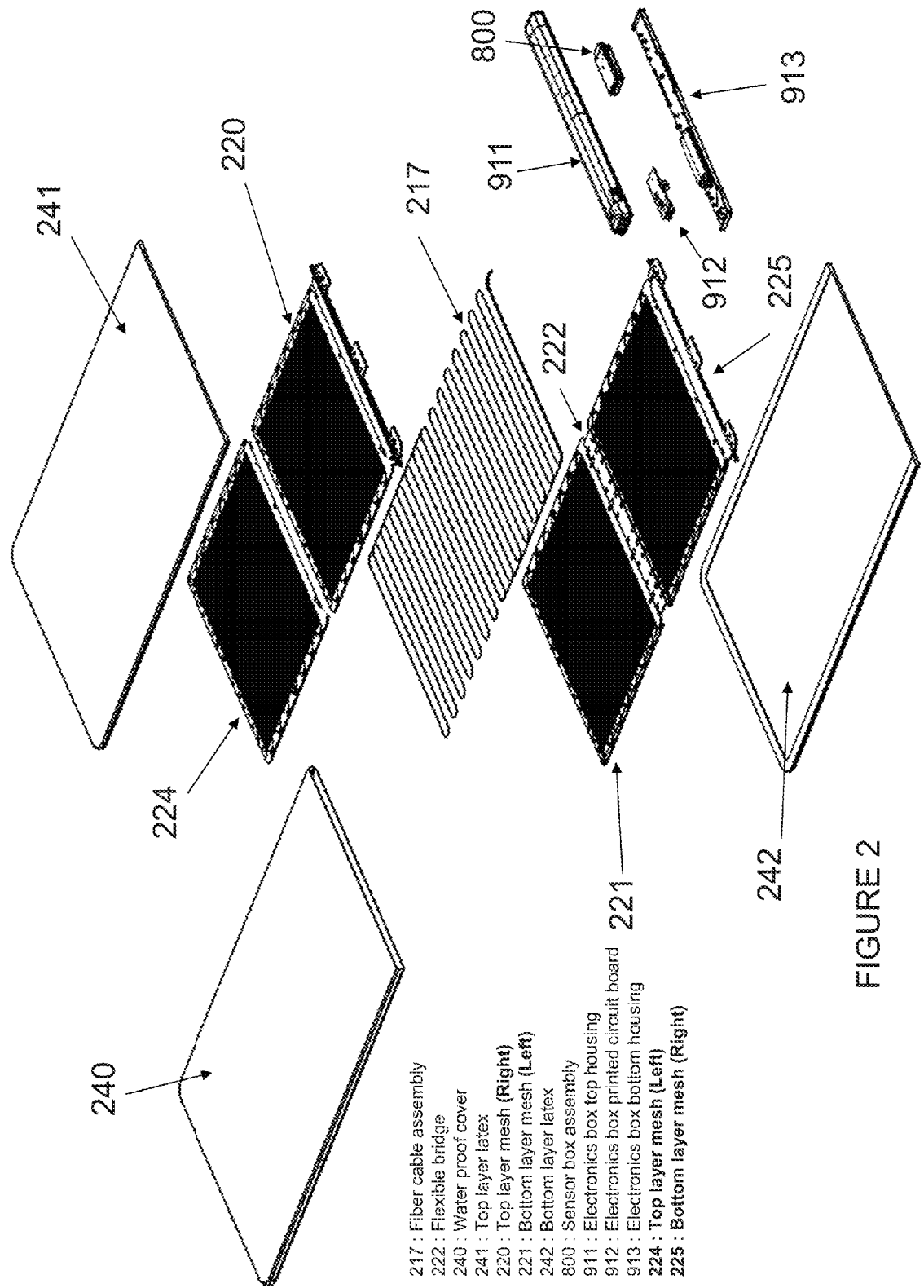
FIG. 2 is the exploded view of a baby monitoring mat in one embodiment of the present invention.

FIG. 2 shows the exploded view of the baby monitoring mat 210 in accordance with one embodiment of the present invention. The central portion is made up of the sensor which includes of optical fiber cable 217 winded in a symmetrical manner with top layer meshes 220,224 and bottom layer meshes 221,225 acting as the optical cable guide to sandwich and secure the optical fiber 217 in place. In the middle of the bottom layer meshes 221,225 and the top layer meshes 220,224, there is a flexible bridge 222 which acts as a hinge which binds all the four portions of the top layer meshes 220,224 and the bottom layer meshes 221,225 together. Besides binding the four meshes together, the main function of the flexible bridge 222 is to enable the baby monitoring mat 210 be foldable so that the baby monitoring mat can be more compact for storage and portable for carrying along with the baby. At the folding edge, the flexible bridge 222 guides the optical fiber cable 217 such that it is not bend at an acute angle that will break the optical fiber cable 217. The top layer mesh 220,224 and bottom layer mesh 221,225 together with the flexible bridge 222 form the mechanism to secure and lock the optical fiber cable 217 in place with the routing pattern defined. The top layer latex 241 and bottom layer latex 242 together with the protective cover 240 is provided to sandwich the meshes with the optical fiber cable 217 embedded to form the sensor mat 210. The sensor mat 210 is attached in place on the Electronic box top housing 911 and Electronic box bottom housing 913. The Electronic box 410 includes of a sensor box assembly 800 and an electronic printed circuit board 912. The optical fiber cable 217 is connected to the sensor box assembly 800, which is the brain that controls the whole baby monitoring mat 210. The electronic printed circuit board 912 housed the power on/off push button, external connections to AC/DC adaptor, alarm and Power LED indication. Electronic box bottom housing 913 also housed compartment enclosure for installation of 4 pieces AA battery.

Figure 3:
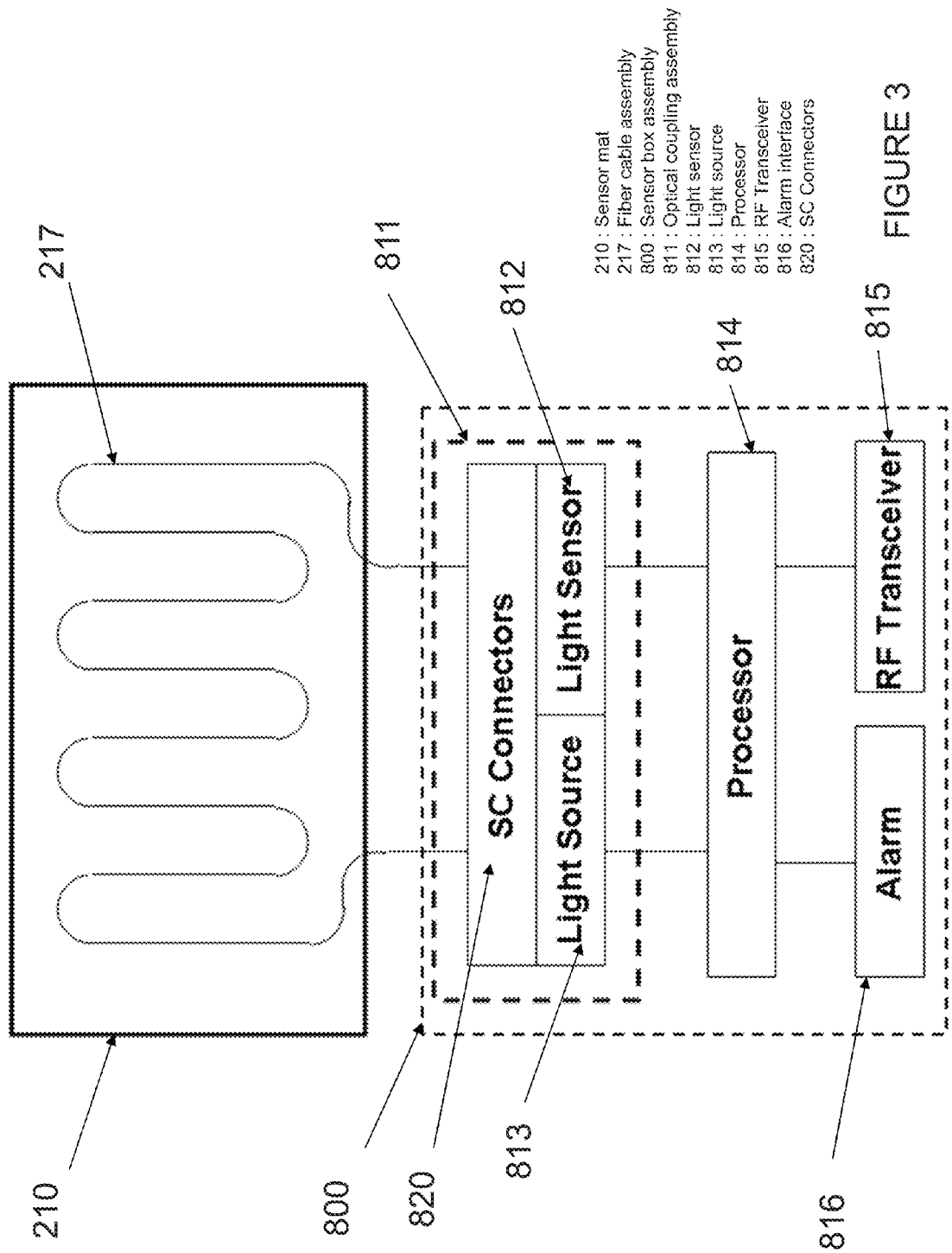
FIG. 3 is the schematic block diagram of a baby monitoring mat in a further embodiment of the present invention.

FIG. 3 illustrates a block diagram of the baby monitoring mat 210 in accordance with another embodiment of the present invention. As shown in FIG. 3, the optical fiber 217 sandwiched within the baby monitoring mat 210 as shown in FIG. 2 is connected to a sensor box assembly 800. This is the sensor from which all critical events are derived. The basic principle of the sensor is based on measurement of light attenuation loss generated by macro bending effect of the optical fiber cable during baby breathing movements. A multimode fiber is used to channel light through relatively tight bends. From a long term mechanical reliability standpoint and to limit light attenuation from bend losses, the bending diameter of the fiber may be limited to be greater than about 20 mm. An optical sensor assembly 811 is adapted for channeling light from a light source 813 as well as detecting light using a light sensor 812 attached at the tail end of the optical fiber. The construction of the light coupling assembly structure enables a standard LED and Photodiode to be embedded such that the optical fiber can be connected to the structure using standard SC connectors 820. 814 illustrates the processor unit, which is the brain behind the differentiation of the signal channeled through the fiber. The reference light source 813 sent into the fiber sensor structure will be modulated by the bending losses created by baby movement which causes light attenuation losses of the light received by the light sensor 812 at the tail end of the optic fiber. The processor analyses the attenuation losses to determine events such as baby presence, movement and breath count. When such events are detected by the processor, it will initiate alarm 816 directly and send the notification wirelessly via the RF transceiver 815 to a Parent Control Unit 310 for alerting the caregiver.

Figure 4:
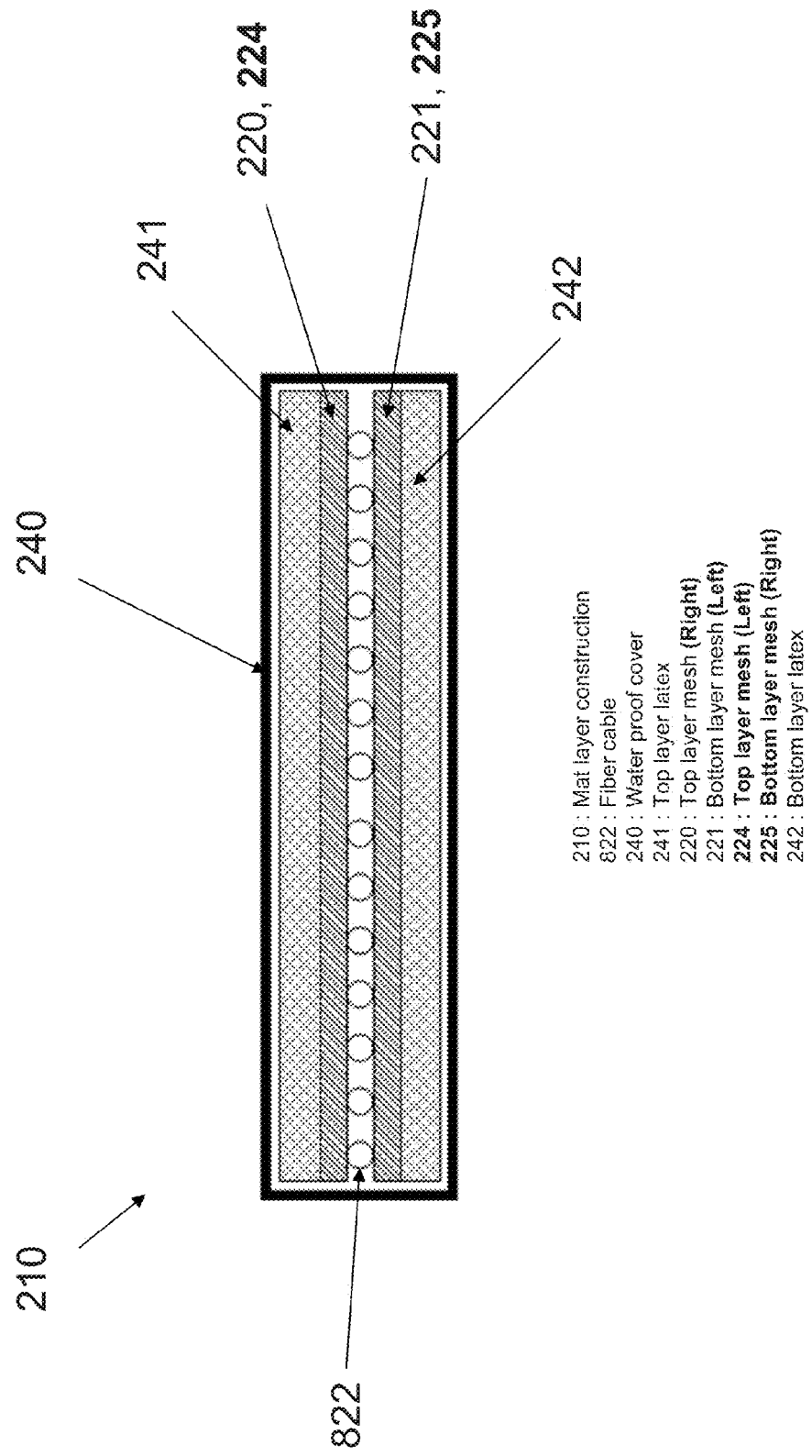
FIG. 4 is the cross section of a sensor mat of FIG. 2.

FIG. 4 illustrates the cross section of the sensor mat 210. The optic fiber 822 is routed in a symmetrical manner space at least about 20 mm apart and sandwiched between two layers of mesh network 220, 224, 221, 225. The mesh network 220, 224, 221, 225 is responsible for generating the bending losses to light passing through the optic fiber caused by the baby's chest movement during sleep. The mesh network 220,221 is sandwiched by latex sheets 241,242 to mask the hardness of the mesh material to allow comfortable feel during baby sleep. The outer layer 240 includes a protective sleeve that uses material that is waterproof, antibacterial, cooling and easy to de-sanitize. This allows baby to directly sleep on top of the mat.

Figure 5:
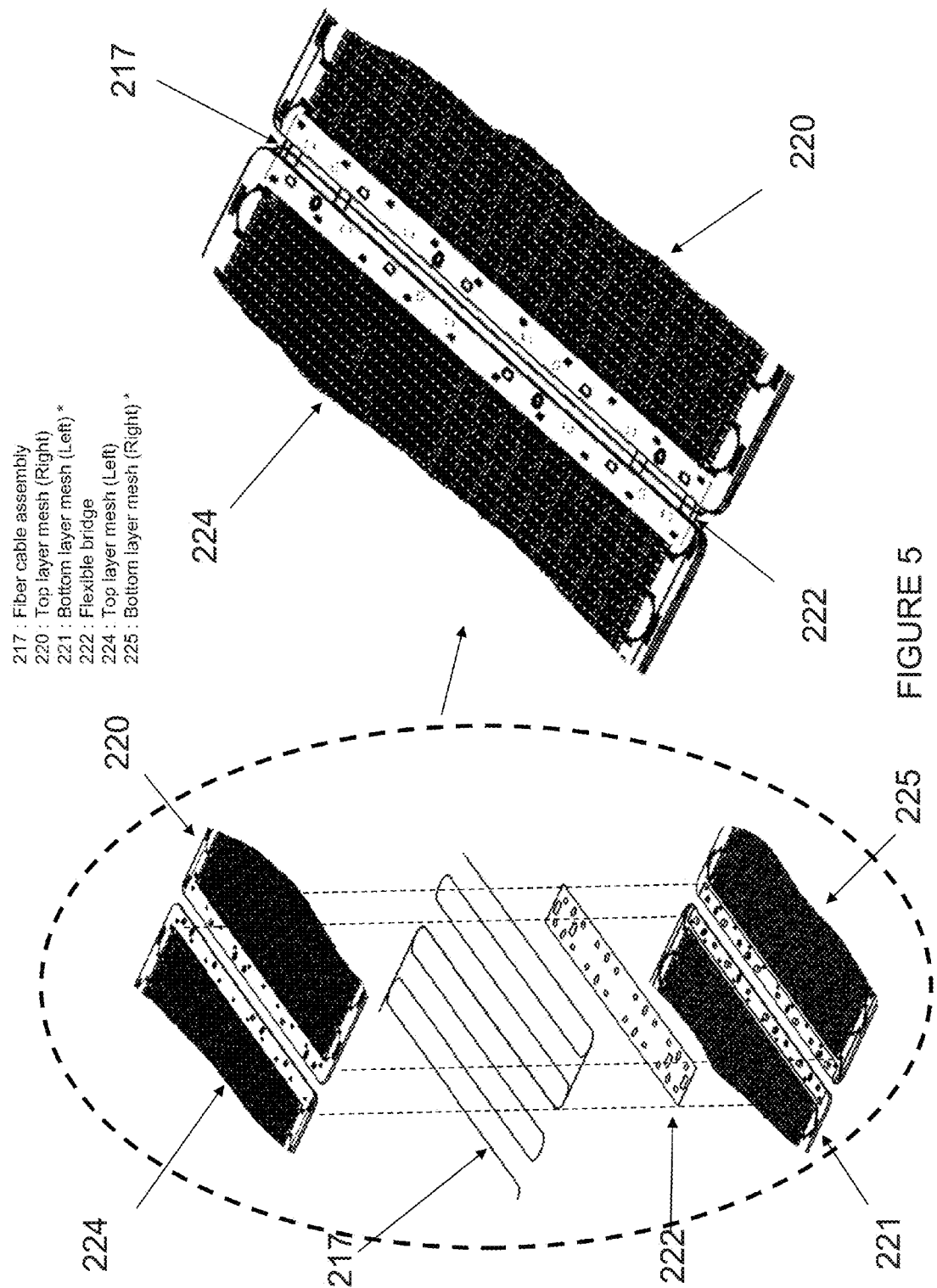
FIG. 5 is the exploded view of the flexible bridge connection to the mesh structure and the optical cable.
Figure 6:
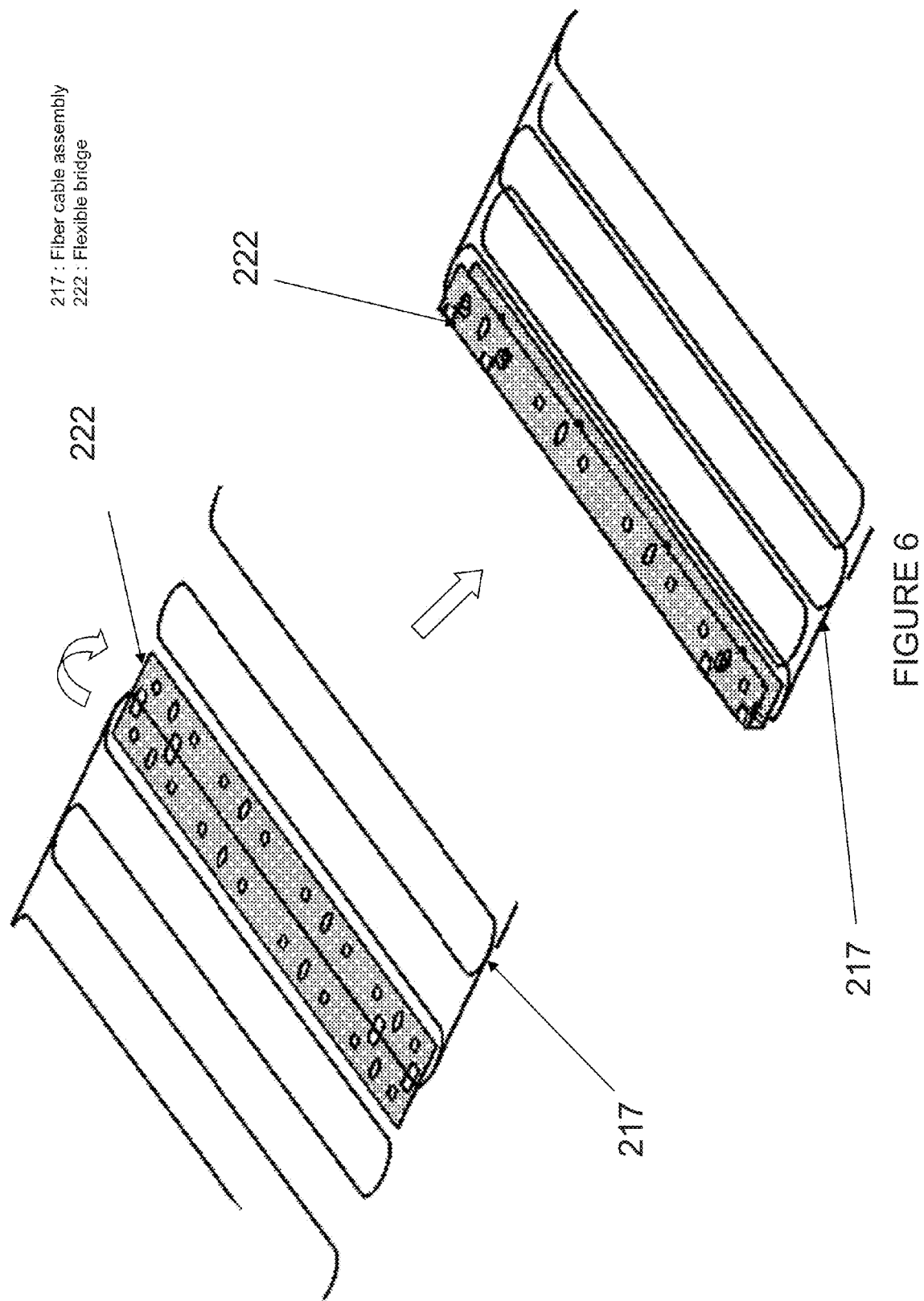
FIG. 6 shows the flexible bridge design together with the optical fiber before and after bending.

FIG. 5 is the exploded view of the flexible bridge connection to the mesh structure and the optical cable in accordance with one embodiment of the present invention. The flexible bridge 222 is made of soft stretchable material such as silicone rubber or similar elastic materials. The flexible bridge 222 is adapted with means to secure the four sides of the mesh 220, 224, 221, 225 together such that the sensor mat 210 is foldable. The other major function of the flexible bridge 222 is to control the bending angle of the fiber cable assembly 217 at the folding area such that the folding angle does not cause any breakage to the fiber cable. FIG. 6 highlights the optical fiber before and after it has been folded. As illustrated, the fiber cable bending angle is controlled by the flexible bridge 222 such that the fiber cable does not break when it is folded.

Figure 7:
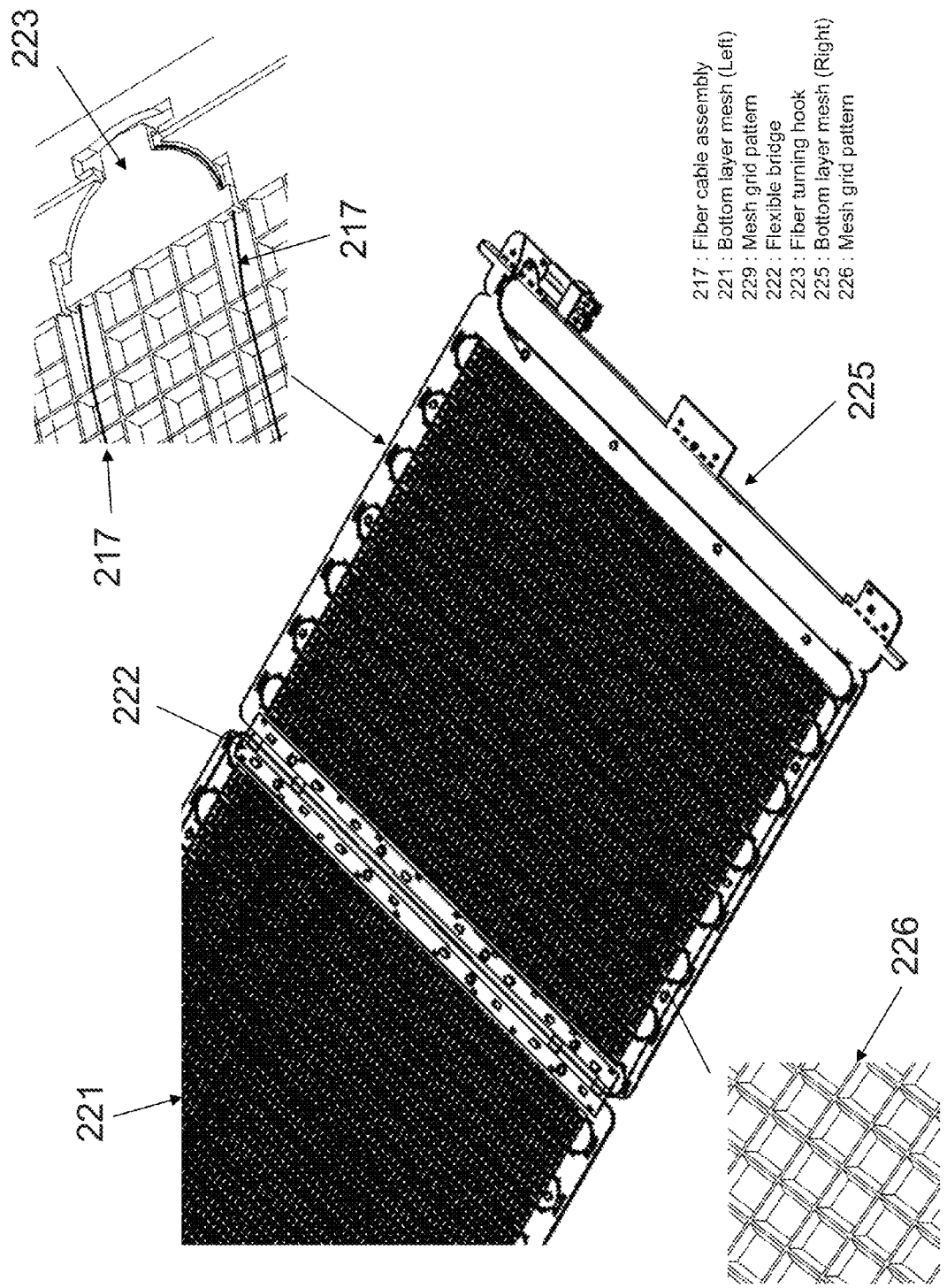
FIG. 7 is a bottom layer mesh of the sensor mat in yet another embodiment of the present invention.

FIG. 7 shows the design of the bottom layer mesh 221,225 that is used to generate macro bending losses to the optic fiber in one embodiment of the present invention. The grid pattern 226 has a spacing of at least about 5 mm and no less than about 8 mm to generate the macro bending effect. The grid pattern 226 exists on the top layer meshes 220,224 and bottom layer meshes 221,225 such that when the optic fiber cable 217 is sandwiched between them, bending losses occurs as the grid edge comes in contact with the fiber cable. The fiber turning hook 223 is used to guide and secure the optical fiber cable as it is laid across the bottom mesh layers 221,225. The fiber turning hook 223 is present at spacing of about 20 mm at both sides of the mesh. This enables optical fiber cable to be easily routed across the entire mesh layer using the fiber turning hook 223 to fix the position of the optic fiber cable 217 pattern. In the middle of the bottom layer meshes 221,225, a flexible bridge 222 is used to secure the two halves of the mesh layers together. The flexible bridge 222 is made of soft material to enable the two halves of the mesh to be folded together.

Figure 8:
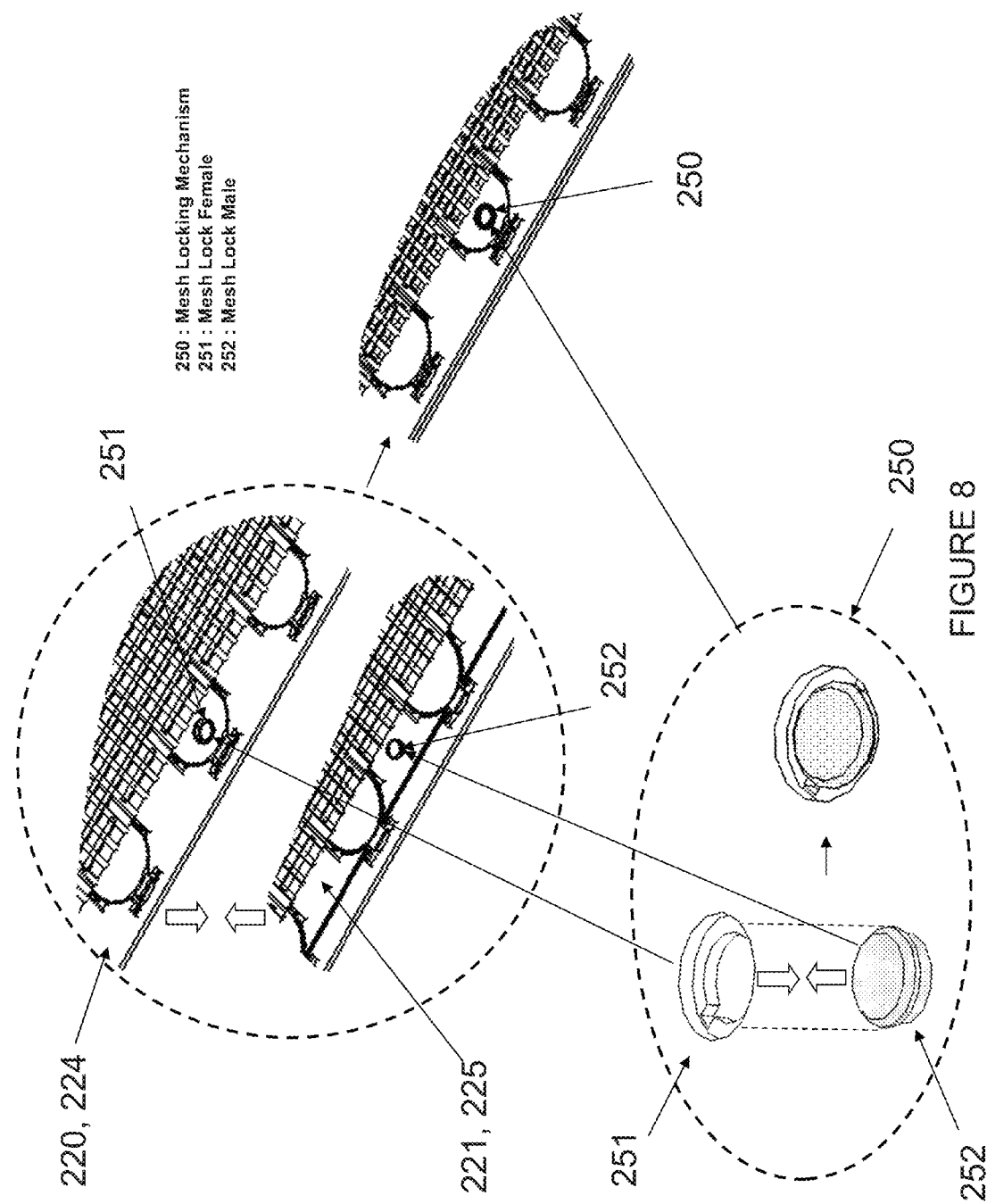
FIG. 8 shows the locking mechanism between the top layer mesh and bottom layer mesh.

FIG. 8 shows the means 250 for securing a top layer mesh with a bottom layer mesh in accordance with one embodiment of the present invention. Both top and bottom layer meshes are provided with coupling through holes along the respective side edge of the meshes 220, 224, 221, 225. The means are adapted with male 252 and female 251 mesh lock stubs that act as the locking mechanism to secure the top layer mesh to the bottom layer mesh through the through holes.

Figure 9:
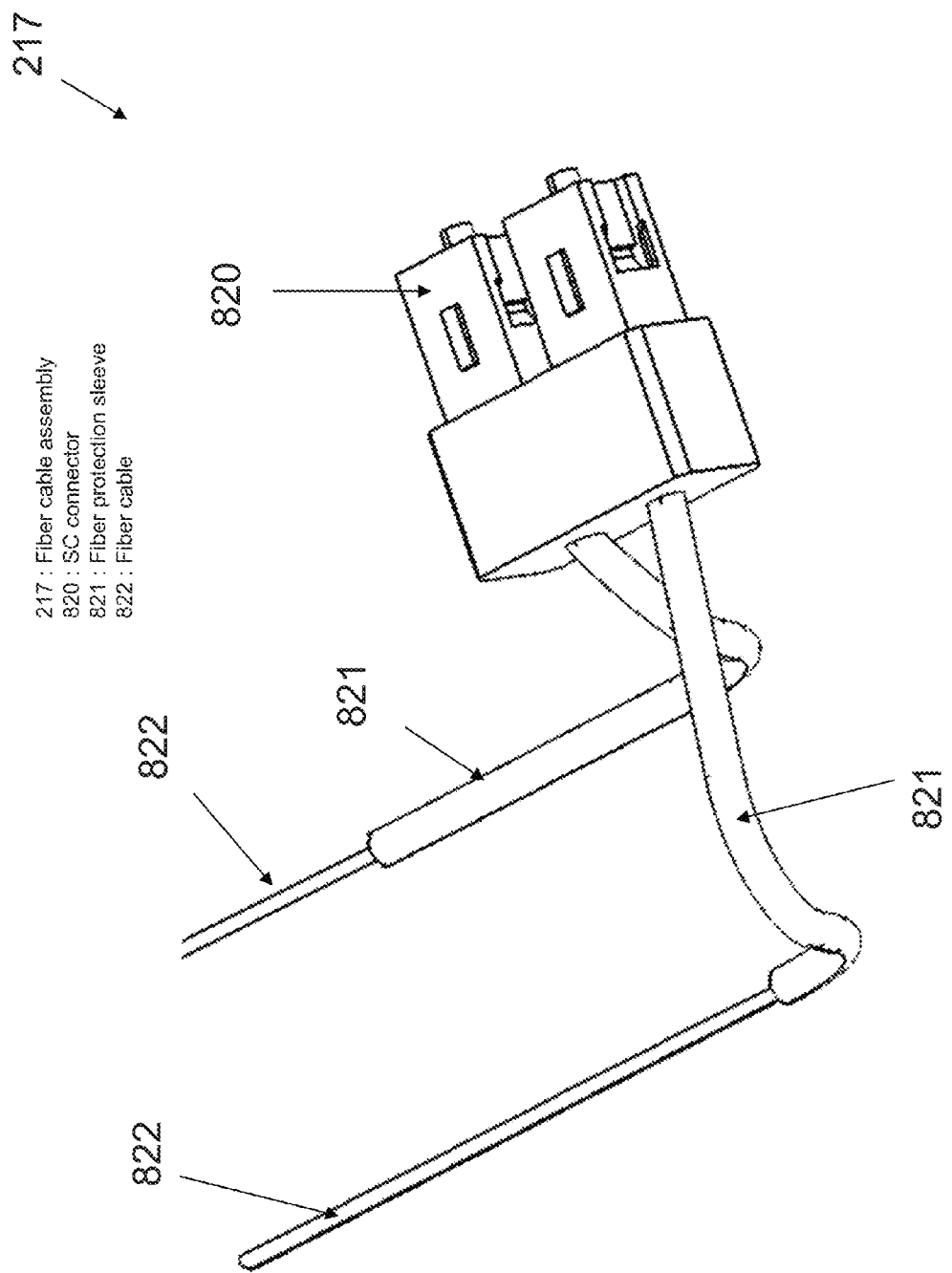
FIG. 9 is an Optical Fiber Cable assembly in an embodiment of the present invention.

FIG. 9 shows the Optical fiber cable assembly 217. The fiber cable 822 is terminated with SC connectors 820. One side of the SC connector 820 pipes the light source into the fiber cable 822 while the other end of the fiber cable 822 is terminated with SC connector 820 that has a light sensor which detects the attenuation losses of light channeling through the fiber cable 822. A Fiber protection sleeve 821 covers a short length from the SC connectors to protect the fiber cable 822 from breaking at the connection point of the fiber cable to the SC connectors.

Figure 10:
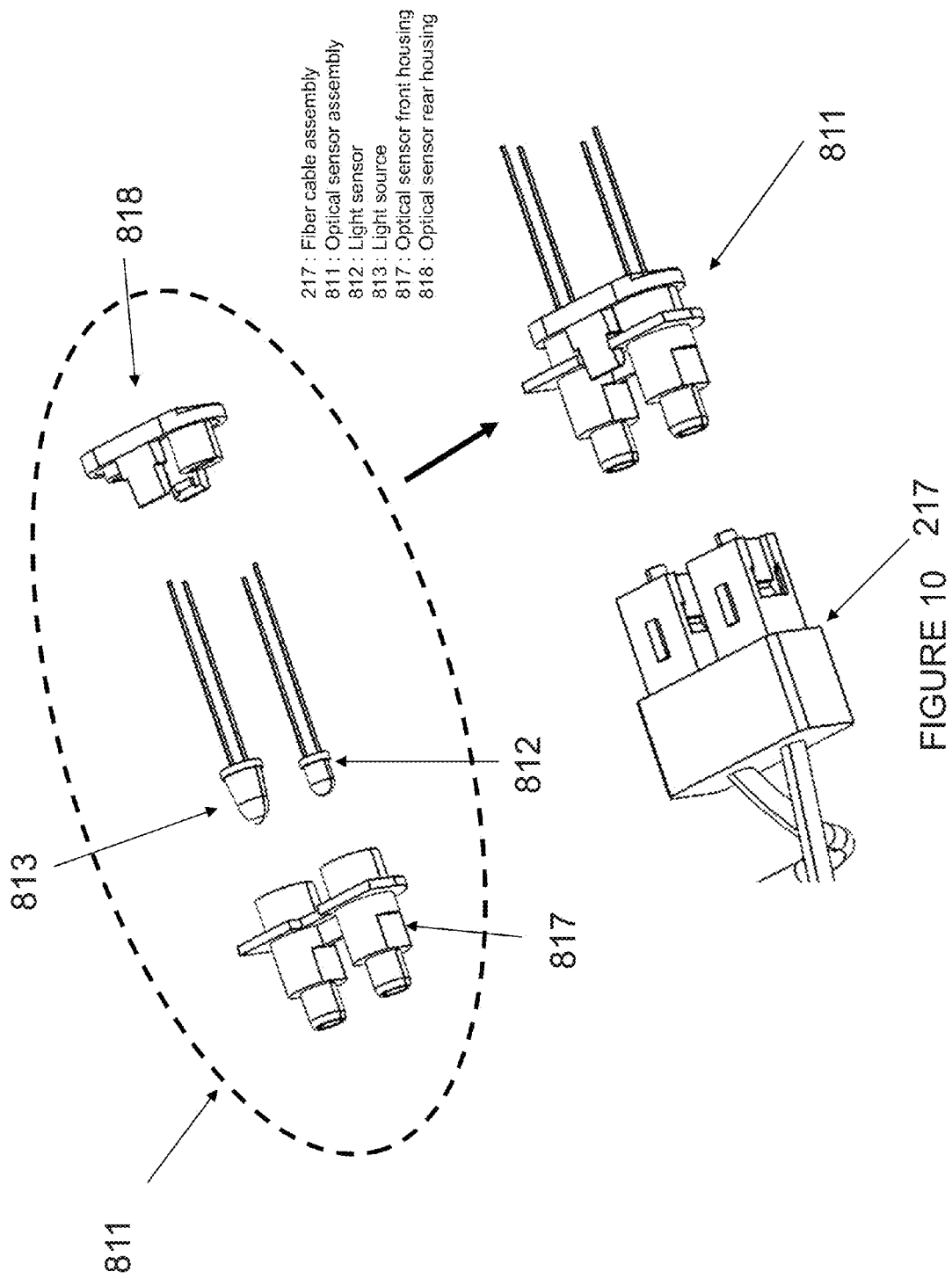
FIG. 10 is an Optical sensor assembly in an embodiment of the present invention.

FIG. 10 shows the exploded view of the optical sensor assembly. The Optical sensor front housing 817 and Optical sensor rear housing 818 has been constructed to house the Light source 813 which is a standard Light Emitting Diode (LED) and a photodiode light sensor 812. The Optical sensor front housing 817 was constructed to act as the male connector side such that the SC connectors 820 of the Optical fiber assembly 217 which is the female side can be plugged in to form the connection with the light source 813 and light sensor 812. The Optical sensor rear housing 818 locks the light sensor 812 and light source 813 into place to form a compact unit that can be mounted into the sensor box assembly 800. The main purpose of the optical sensor assembly is to house both the light source 813 and light sensor 812 such that the fiber cable assembly that uses standard SC connectors 820 can be mated seamlessly with minimal light coupling losses.

Figure 11:
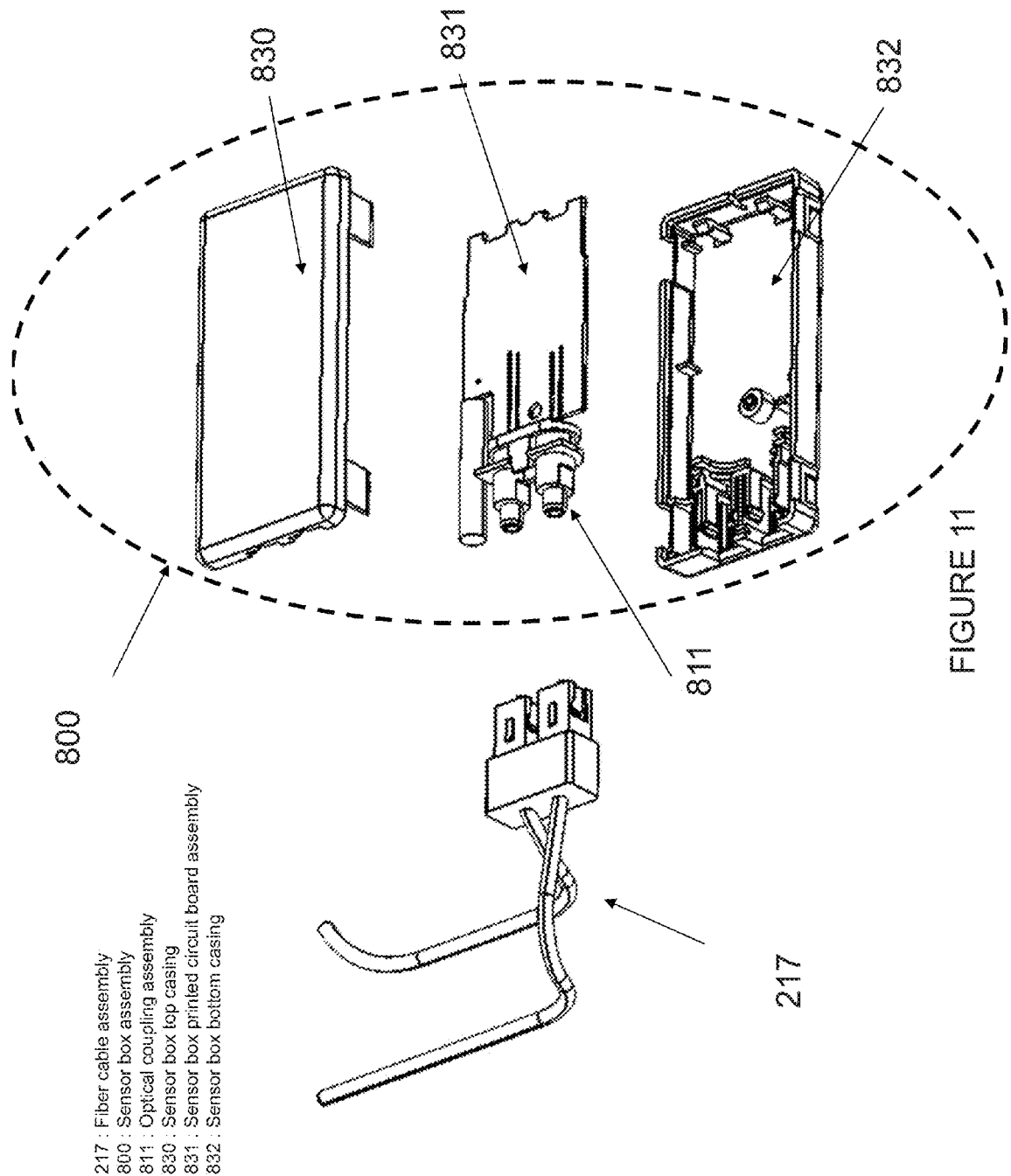
FIG. 11 shows an Optical Fiber Cable assembly of FIG. 9 and an Optical Sensor assembly of FIG. 10 that are assembled for coupling to each other.

FIG. 11 shows the Sensor box assembly 800. The Sensor box assembly 800 includes of three parts. The Sensor box top casing 830 and the Sensor box bottom casing 832 and the Sensor box printed circuit 831. The sensor box top casing 830 and the sensor box bottom casing 832 are adapted to mount the sensor box printed circuit 831 board assembly into place. The optical sensor assembly 811 is soldered to the Printed circuit board that includes the Processor 814, RF Transceiver 815 and Alarm interface 816. The Fiber cable assembly 217 is finally terminated at the Sensor box assembly 800.

Optical fiber cable embedded within the mat is used for sensing movements utilizing a variety of scheme. The method used here is based on bending of non-coherent light source, which can be common light emitting diodes, coupled into multimode optical fiber travelling along the length of the fiber optic cable. When optical fiber cable is bent, there is light lost from the fiber due to internal reflections. The movement of the baby on top the mat will cause distinct light bending lost pattern. By measuring the light bending lost pattern at the receiver end of the optical fiber cable, detection of movement, breath count and presence can be differentiated.

The construction of a baby monitoring mat with optical fiber embedded therein may include a some of the following factors.

First, the optical fiber is brittle and will break when bend at an acute angle. Accordingly, the mesh layer is provided with grid patterns to guide and protect the optical fiber from any damage due to the bending. Further, the flexible bridge joining up the two separate mesh layer is also adapted to guide and protect the optical fiber damage even when the baby monitoring mat is folded up.

Second, the sensitivity of the mat depends on how the optical fiber cable is routed and secured in the sensing mat. Considering the first factor, the grid patterns shall also be adapted properly to optimize the sensitivity as much as possible. As shown in FIGS. 4 and 7, the optical cable is spaced at least about 20 mm, for example, apart to prevent light loss at the bending corner, which will affect the sensitivity. Further, the mesh layer grid pattern has a gap of at least about 5 mm and less than 8 mm to ensure optimal light attenuation loss when the fiber comes in contact with the grid at regular intervals. Operationally, multiple bending of the optical cable would generate strong baby movement signal because the light attenuation loss is larger.

Third, the configuration of a sandwiched structure that creates bending effect for the optic fiber is critical to the sensitivity of the mat. Embodiments of the sandwiched structure are shown in FIGS. 2 and 4. In these figures, the top and bottom mesh layer forms the main sandwiched structure where the latex layers offer comfort.

Fourth, the coupling of light for the transmitter and receiver is subject to coupling losses, which affect the signal strength at the receiver end. Accordingly, proper construction of the system and connections is necessary to avoid light loss. The coupling configurations are shown in FIGS. 9 and 10.

And fifth, the sensing mat may be able to derive good signal strength for a light weight baby of minimum 1.5 Kg in order to decipher the received data for event detection. The sensor box assembly also includes an electronic sensor board mounted with a 16 bit low noise, high resolution ADC converter used to extract the necessary signals with sufficient Signal-to-Noise ratio to distinguish the different events, such as baby presence/absence, movement and breath count.

Figure 12:
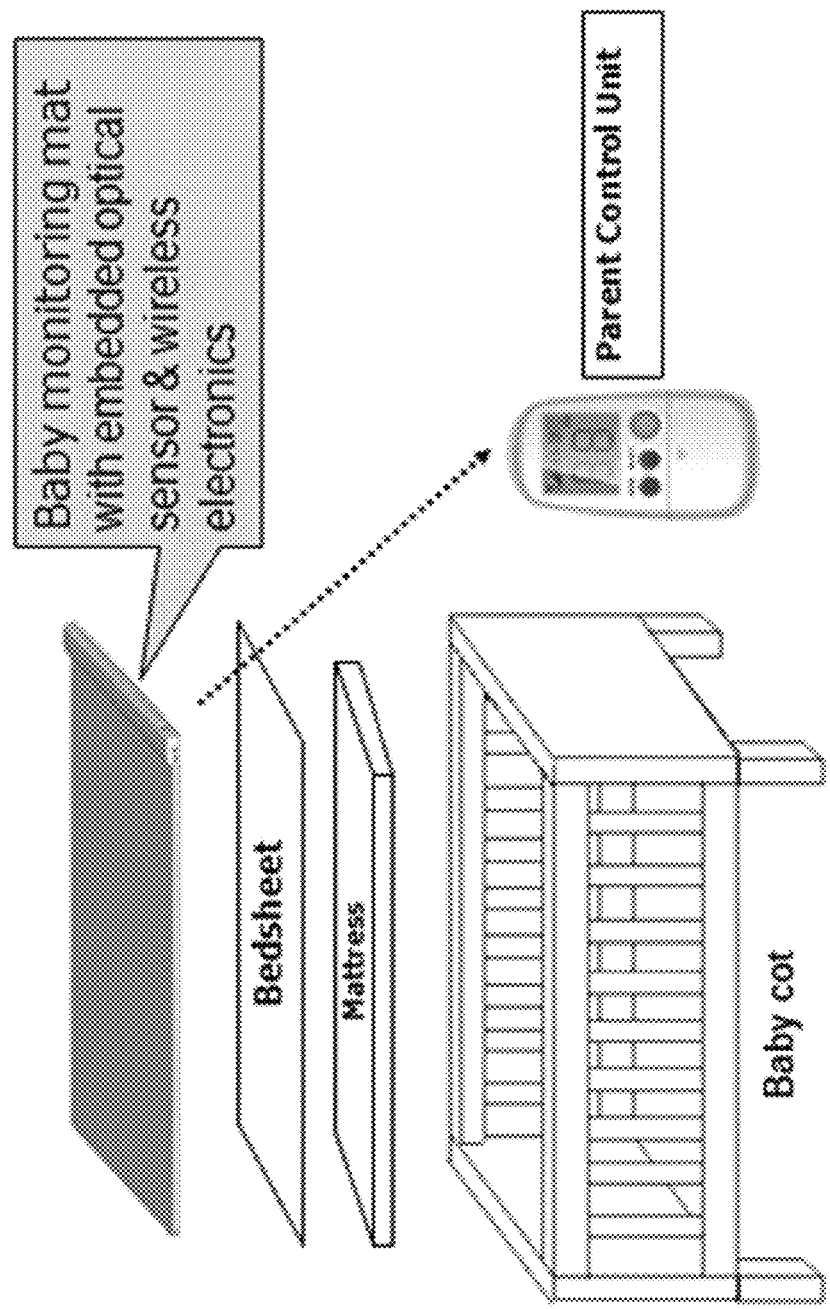
FIG. 12 is an illustration of baby monitoring mat when used in a baby cot.

FIG. 12 shows an application of the baby monitoring mat 210 in one embodiment of the present invention. The current invention includes of a baby monitoring mat 210 that acts as the sensor that continuously monitors the baby when he/she lies on top. A Parent Control Unit 310, wirelessly connected with the baby monitoring mat 210, acts as an indicator that alarms the caregiver when the baby mat detects baby out of mat, baby wakes up from sleep and baby breath count is zero while on mat 210. When zero baby breath count is detected, a stimulation device that is worn on one of the baby's feet will vibrate to jolt the baby to re-initiate its breathing pattern while parent is notified to tend to the baby.

As shown in FIG. 12, the baby monitoring mat 210 is placed on top of a mattress 212 of a baby cot 214. A bed sheet 216 may be placed beneath the baby monitoring mat 210 to protect the mattress. When in used, the baby is placed on top on the baby monitoring mat 210.

FIGS. 13 to 16 exemplify signals patterns that represent the various movements and breath counts.

The present invention is applicable towards the prevention or at least reduction of sudden infant death syndrome (SIDS) by monitoring baby's respiration and if the baby stops breathing, awaken the baby using external stimulation attached to baby's feet. The use of Fiber Optic Sensor enables a non intrusive way of detecting the baby's respiration without any cable/probes/sensor attached to the baby's skin. The baby monitoring mat starts monitoring movement and respiratory sign when the baby sleeps on it.

The above description illustrates various embodiments of the present invention along with examples of how aspects of the present invention may be implemented. While specific embodiments have been described and illustrated it is understood that many changes, modifications, variations and combinations thereof could be made to the present invention without departing from the scope of the present invention. The above examples, embodiments, instructions semantics, and drawings should not be deemed to be the only embodiments, and are presented to illustrate the flexibility and advantages of the present invention as defined by the following claims.

The invention claimed is:

1. A Baby Monitoring Mat, comprising:
   a sensor mat having a top mesh layer, a bottom mesh layer, and two flexible sheets and an optical cable, wherein the optical cable is routed across and sandwiched in between the top mesh layer and the bottom mesh layer, and the flexible sheets further sandwiched the top mesh layer and the bottom mesh layer in between forming sensing area across the flexible sheet surface;
   a light source for feeding light from one side of the optical cable;
   wherein the light source is a light emitting diode;
   a photodiode for detecting light attenuation at the other end of the optical cable;
   a printed circuit board having a processor connected to the light source and the photodiode, wherein the processor operationally receives signals from the photodiode, the signals are processed to determine movements and breath counts,
   wherein the signals are generated based on the light attenuation changes along the optical cable detected by photodiode, the light attenuation changes are operationally caused by the optical cable bending in response to the movements and breath.

2. The Baby Monitoring Mat according to claim 1, wherein the flexible sheets are latex sheets.

3. The Baby Monitoring Mat according to claim 1, wherein the optical cable is a multimode optical fiber cable.

4. The Baby Monitoring Mat according to claim 3, wherein the top and bottom mesh layer comprises grid patterns adapted to guide and protect the multimode optical fiber cable routed in a symmetrical manner across the sensor mat.

5. The Baby Monitoring Mat according to claim 4, wherein the multimode optical fiber cable is spaced at least about 20 mm apart.

6. The Baby Monitoring Mat according to claim 4, wherein top and bottom layer of mesh comprises symmetrical grid pattern spaced at least about 5 mm and less than about 8 mm apart with fiber turning hooks with spacing of 20 mm apart to guide the multimode optical fiber across the sensor mat.

7. A Baby Monitoring Mat comprising:
- a sensor mat having a top mesh layer, a bottom mesh layer, and two flexible sheets and an optical cable, wherein the optical cable is routed across and sandwiched in between the top mesh layer and the bottom mesh layer, and the flexible sheets further sandwiched the top mesh layer and the bottom mesh layer in between forming sensing area across the flexible sheet surface;
- a light source for feeding light from one side of the optical cable;
- a photodiode for detecting light attenuation at the other end of the optical cable;
- a printed circuit board having a processor connected to the light source and the photodiode, wherein the processor operationally receives signals from the photodiode, the signals are processed to determine movements and breath counts; and
- a flexible bridge for connecting two sandwiched mesh layers for allowing the Baby Monitoring Mat to be foldable;
- wherein the signals are generated based on the light attenuation changes along the optical cable detected by photodiode, the light attenuation changes are operationally caused by the optical cable bending in response to the movements and breath.

8. The Baby Monitoring Mat according to claim 7, further comprising a wireless transceiver on the printed circuit board, wherein the wireless transceiver operably transmits status information such as baby presence, movement and breath counts, to a remote display unit, such that the movements on the sensor mat can be monitored there through.

9. A Baby Monitoring Mat comprising:
- a sensor mat having a top mesh layer, a bottom mesh layer, and two flexible sheets and an optical cable, wherein the optical cable is routed across and sandwiched in between the top mesh layer and the bottom mesh layer, and the flexible sheets further sandwiched the top mesh layer and the bottom mesh layer in between forming sensing area across the flexible sheet surface;
- a light source for feeding light from one side of the optical cable;
- a photodiode for detecting light attenuation at the other end of the optical cable;
- a printed circuit board having a processor connected to the light source and the photodiode, wherein the processor operationally receives signals from the photodiode, the signals are processed to determine movements and breath counts; and
- a baby wake up sock electrically connected to the printed circuit board, the wake up sock is wearable on a baby's leg, wherein the wake up sock vibrates when the sensor detects zero breath count when a baby is presence on the sensor mat;
- wherein the signals are generated based on the light attenuation changes along the optical cable detected by photodiode, the light attenuation changes are operationally caused by the optical cable bending in response to the movements and breath.

* * * * *